(12) United States Patent
Liu (10) Patent No.: US 7,847,111 B2
(45) Date of Patent: Dec. 7, 2010

(54) SEMI-SYNTHETIC ROUTE FOR THE PREPARATION OF PACLITAXEL, DOCETAXEL, AND 10-DEACETYLBACCATIN III FROM 9-DIHYDRO-13-ACETYLBACCATIN III

(75) Inventor: Jian Liu, Fredericton (CA)

(73) Assignee: Canada Inc., Montreal, QC (CA)

( * ) Notice: Subject to any disclaimer, the term of this patent is extended or adjusted under 35 U.S.C. 154(b) by 1007 days.

(21) Appl. No.: 11/425,034

(22) Filed: Jun. 19, 2006

(65) Prior Publication Data

US 2007/0293687 A1    Dec. 20, 2007

(51) Int. Cl.
*C07D 305/14*    (2006.01)

(52) U.S. Cl. ...................................... 549/510; 549/511
(58) Field of Classification Search .................. 549/510, 549/511
See application file for complete search history.

(56) References Cited

U.S. PATENT DOCUMENTS

| | | | |
|---|---|---|---|
| 4,924,011 A | 5/1990 | Denis et al. | |
| 5,352,806 A | 10/1994 | Gunawardana et al. | |
| 5,440,056 A | 8/1995 | Klein et al. | |
| 5,530,020 A | 6/1996 | Gunawardana et al. | |
| 5,594,157 A | 1/1997 | Gunawardana et al. | |
| 5,616,740 A | 4/1997 | Klein et al. | |
| 5,763,477 A | 6/1998 | Duvvuri et al. | |
| 6,066,747 A | 5/2000 | Holton et al. | |
| 6,175,023 B1 | 1/2001 | Liu | |
| 6,197,981 B1 | 3/2001 | Liu | |
| 6,222,053 B1 | 4/2001 | Zamir et al. | |
| 6,232,477 B1 | 5/2001 | Bouchard et al. | |
| 6,331,635 B1 | 12/2001 | Bouchard et al. | |
| 6,384,071 B2 | 5/2002 | Bouchard et al. | |
| 6,495,701 B1 | 12/2002 | Matsubara | |
| 6,552,205 B1 * | 4/2003 | Holton et al. | 549/510 |
| 6,576,777 B2 | 6/2003 | Zamir et al. | |
| 6,593,482 B2 | 7/2003 | Bouchard et al. | |
| 6,706,896 B1 * | 3/2004 | Holton et al. | 549/214 |
| 6,710,191 B2 | 3/2004 | Holton et al. | |

(Continued)

FOREIGN PATENT DOCUMENTS

CA    2215682    9/1996

(Continued)

OTHER PUBLICATIONS

Appendino et al, Terta. Let. vol. 38 No. 24 pp. 4273-4276 (1997) "Synthesis and Evaluation of C-Seco Paclitaxel Annalogues".*

(Continued)

*Primary Examiner*—Janet L. Andres
*Assistant Examiner*—Raymond Covington
(74) *Attorney, Agent, or Firm*—Benoît & Côté, s.e.n.c.

(57) ABSTRACT

A semisynthetic route has been provided in the preparation of docetaxel and paclitaxel. This new process involves the conversion of 9-dihydro-13-acetylbaccatin III to docetaxel and paclitaxel by the step of converting 9-dihydro-13-acetylbaccatin III into 7-O-triethylsilyl-9,10-diketobaccatin III, and adding docetaxel and paclitaxel side chain precursors, respectively, to form a new class of taxane intermediates, such as 7-O-triethylsilyl-9,10-diketodocetaxel and 7-O-triethylsilyl-9,10-diketopaclitaxeltaxel. These new intermediates then by a series reduction, acetylation of the 10-hydroxyl position for paclitaxel and finally deprotection to yield docetaxel and paclitaxel, the most important anti-cancer drugs.

40 Claims, 4 Drawing Sheets

U.S. PATENT DOCUMENTS

| | | | |
|---|---|---|---|
| 6,734,304 | B2 | 5/2004 | Weintritt |
| 6,784,304 | B2 | 8/2004 | Tothathil et al. |
| 6,812,356 | B2 | 11/2004 | Findlay et al. |
| 6,872,842 | B2 * | 3/2005 | Holton et al. ............... 549/510 |
| 6,878,834 | B2 * | 4/2005 | Holton et al. ............... 549/510 |
| 7,202,370 | B2 * | 4/2007 | Naidu ........................ 549/510 |

FOREIGN PATENT DOCUMENTS

| | | |
|---|---|---|
| CA | 2231837 | 3/1997 |
| CA | 2188190 | 4/1998 |
| CA | 2307548 | 11/1998 |
| CA | 2403429 | 9/2001 |
| CA | 2444693 | 3/2004 |
| EP | 0400971 | 12/1990 |
| EP | 0428376 A1 | 5/1991 |
| WO | WO 2005/030150 | 4/2005 |
| WO | WO 2007/073383 | 6/2007 |
| WO | WO 2005/075870 | 7/2007 |

OTHER PUBLICATIONS

Appendino G et al: "The Reductive Fragmentation of 7-Hydroxy-9,10-dioxotaxoids" European Journal Oforganic Chemistry, Wiley-VCH Verlag, Weinheim, DE, No. 22, Jan. 1, 2003, pp. 4422-4431, XP002486097 ISSN: 1434-193X scheme 4; p. 4426.

Denis J-N: "A Highly Efficient~Practical 7-14 Approach Tonatural Taxol" Journal of the American Chemical Society, vol. 110, No. 17, 1988, pp. 5917-5920, XP000654163; ISSN: 0002-7863 ; p. 5918; compound 4.

EPO—Supplementary European Search Report—EP 07719967—(EPO Form 1503 03.82)—Nov. 2, 2009—11 pages.

PCT—International Search Report (ISR)—PCT/CA2007/001051 (Form PCT/ISA/210)—Oct. 4, 2007—4 pages.

* cited by examiner 1
9-dihydro-13-acetylbaccatin III 2
10-deacetylbaccatin III

3
Paclitaxel

4
Docetaxel

SEMI-SYNTHETIC ROUTE FOR THE PREPARATION OF PACLITAXEL, DOCETAXEL, AND 10-DEACETYLBACCATIN III FROM 9-DIHYDRO-13-ACETYLBACCATIN III

BACKGROUND OF THE INVENTION (a) Field of the Invention

The present invention relates to a semi-synthetic process for the preparation of paclitaxel, docetaxel, the anticancer drugs, and 10-deacetylbaccatin III, a useful precursor for making them, the most popular anticancer drugs, and other taxane compounds. More particularly, this invention relates to a novel semi-synthetic route to synthesize paclitaxel, docetaxel and 10-deacetylbaccatin III from 9-dihydro-13-acetyl-baccatin III, a taxane compound which is isolated from *Taxus Canadensis*, an evergreen bush found in Eastern Canada and Northeastern United States.

(b) Description of Prior Art

Taxanes are substances occurring naturally in yew trees such as *Taxus brevifolia, Taxus baccata* and *Taxus canadensis*, which is common in Eastern Canada and Northeast United States. One of the chemicals extracted from the needles of *Taxus canadensis* is 9-dihydro-13-acetylbaccatin III, which is used to produce 10-deacetylbaccatin III, a useful intermediate for the preparation of paclitaxel, docetaxel and their analogues thereof.

The taxane family of diterpenes is considered to be an exceptionally promising group of cancer chemotherapeutic agents. Many taxane derivatives, including paclitaxel, docetaxel, taxol C and cephalomannine are highly cytotoxic and possess strong in vivo activities in a number of leukemic and other tumor systems. Paclitaxel, and a number of its derivatives, have been shown to be effective against advanced breast and ovarian cancers in clinical trials. They have also exhibited promising activity against a number of other tumor types in preliminary investigations. Paclitaxel, docetaxel have recently been approved in the U.S. and Canada for the treatment of ovarian and breast cancers.

The only available natural source of paclitaxel to date are several species of a slow growing yew trees (genus *Taxus*), wherein paclitaxel is found in very low concentrations (less than 400 parts per million) in the bark or needles of these trees. Thus, paclitaxel can be isolated from the bark of the pacific yew tree (*Taxus brevifolia*) and ground hemlock (*Taxus Canadensis*), but the yield is very low (0.01%-0.02%), and the isolation and purification process is too complicate. Furthermore the extraction is difficult, and the process is expensive. Since removal of the bark destroys the trees and endangers the species, isolation of taxanes from the stems and needles of various *Taxus* species was believed to offer hope that the supply of taxanes, in particular paclitaxel, would become more abundant. This led to the switching of paclitaxel derived from natural to the production of semi-synthetic, starting from 10-deacetylbaccatin III, which was isolated from the needles of English yew (*Taxus baccata*).

Due to the structural complexity of paclitaxel, and docetaxel, partial synthesis is a far more viable approach to providing adequate supplies of paclitaxel and docetaxel. Docetaxel was first commercialized by Aventis, It went to the market in 1995 and it is a fast growing anticancer drug. This drug is semi-synthetic product, also starting from 10-deacetylbaccatin III. So far the commercial supply of docetaxel comes substantially completely from 10-deacetylbaccatin III. To date, however, the supply of 10-deacetylbaccatin III is limited due to the limited biomass resource and low isolation yield (ranging from 50-165 mg per kilogram of needles of *Taxus baccata*).

Various processes of converting 9-dihydro-13-acetylbaccatin III (9-DHAB) into 10-deacetylbaccatin III have been proposed. However, it has been found that such processes result in poor yields of final product. Thus, a need still exists for an efficient method for converting 9-dihydro-13-acetyl-baccatin III to 10-deacetylbaccatin III (10-DAB III).

The preparation of paclitaxel derivatives, some of which have been reported to demonstrate enhanced chemotherapeutic activity, ultimately depends upon the supply of the precursor compound, namely, 10-deacetylbaccatin III (10-DAB III). The structure of 10-DAB III has the basic diterpenoid structure of paclitaxel without the acetyl group at C-10 and side chain at the C-13 position.

Since 10-DAB III is an important staring material in paclitaxel semi-synthesis, the significance of 10-DAB III will likely increase as more clinical studies are performed using paclitaxel. One such reason is that it appears that water-soluble paclitaxel-like compounds with slightly modified C-13 side chains may be more desirable as cancer chemotherapeutic agents than the naturally-occurring, less water soluble paclitaxel. This increases the urgent need for the production of 10-DAB III as a starting material to synthesize both paclitaxel and second or third generation paclitaxel-like compounds. There is, therefore, a need for an improved method of isolating and/or synthesizing 10-DAB III.

In fact, most of the research to date regarding the semi-synthesis of paclitaxel has involved 10-deacetylbaccatin III. The conversion of 10-deacetylbaccatin III into paclitaxel is typically achieved by protecting the hydroxy at C-7, attachment of an acetyl group at the C-10 position, attachment of a C-13 β-amido ester side chain at the C-13 position through esterification of the C-13 alcohol with the side chain moiety, and deprotecting C-7. Since the supply of 10-deacetylbaccatin III is limited, other sources should be pursued.

Canadian Patent Application No. 2,188,190, published on Apr. 18, 1998, in the name of Zamir et al, described a semi-synthetic process to convert a naturally occurring taxane, 9-dihydro-13-acetylbaccatin III, into a suitable starting material for the synthesis of such taxane derivatives as paclitaxel, cephelomanine and other taxanes, which are structurally related to baccatin III.

U.S. Pat. No. 6,812,356, issued on Nov. 2, 2004, in the name of Findly, provided a process for the use of 9-dihydro-13-acetylbaccatin III for the production of 10-deacetylbaccatin III.

U.S. Pat. No. 6,784,304, issued on Aug. 31, 2004, in the name of Bristol-Myers Squibb Company provided novel oxazolidines, which found utility as intermediates in the preparation of C-13 side chain-bearing taxanes, e.g., paclitaxel and analogs thereof. It related more specifically to procedures for coupling the oxazolidines to form taxanes.

U.S. Pat. No. 6,710,191, issued on Mar. 23, 2004 in the name of R. A. Holton et al, provided a process for the preparation of a derivative or analog of baccatin III, or 10-deacetyl-baccatin III, having a C9 substituent other than a keto, in which the C9 keto substituent of taxol, a taxol analog, baccatin III, or 10-deacetylbaccatin III was selectively reduced to the corresponding hydroxyl group.

U.S. Pat. No. 6,593,482, issued on Jul. 15, 2003 in the name of H. Bouchard et al, provided a procedure for preparing methylthiomethyl taxoids from baccatin III and β-lactam.

U.S. Pat. No. 6,576,777, issued on Jun. 10, 2003 in the name of L. Zamir et al, provided a semi-synthetic process to convert a naturally occurring taxane into a suitable starting compound for the synthesis of paclitaxel and related compounds. It specifically related to a process for the conversion of 9-dihydro-13-acetylbaccatin III into a 7-protected baccatin III, which can be used for the synthesis of taxol derivatives, e.g., paclitaxel, docataxel, cephalomannine and other taxanes, which were structurally related to baccatin III.

Other patents which provided processes for the preparation of novel taxoids included U.S. Pat. No. 6,384,071 issued on May 7, 2002 in the name of Aventis Pharma S.A, U.S. Pat. No. 6,331,635 issued on Dec. 18, 2001, in the name of Aventis Pharma S.A. and U.S. Pat. No. 6,232,477 issued on May 15, 2001 in the name of Aventis Pharma S.A.

U.S. Pat. No. 6,222,053, issued on Apr. 24, 2001, in the name of Institut National de la Research Scientific, provided a semi-synthetic process to convert a naturally occurring taxane into a suitable starting material for the synthesis of paclitaxel and related compounds. Specifically, it related to a process for the conversion of 9-dihydro-13-acetylbaccatin III into a 7-protected baccatin III, which can then be used as starting material for the synthesis of such taxane derivatives as paclitaxel, docetaxel, cephalomannine and other taxanes structurally related to baccatin III.

U.S. Pat. No. 6,197,981, issued on Mar. 6, 2001, in the name of J. Liu, provided a process for preparing taxol, baccatin III and 10-deacetylbaccatin III by oxidation of 9-dihydro-13-acetylbaccatin.

U.S. Pat. No. 6,175,023, issued on Jan. 16, 2001 in the name of J. Liu, provided for the semi-synthesis of 9-dihydro-taxanes using 9-dihydro-13-acetylbaccatin III as the initial compound.

U.S. Pat. No. 6,066,747, issued on May 23, 2000 in the name of R. H. Holton et al, provided a process for the preparation of taxol, baccatin III and 10-deacetylbaccatin III derivatives or other taxanes having new C9 functional groups.

U.S. Pat. No. 5,616,740, issued on Apr. 1, 1997 in the name of Abbott Laboratories, U.S. Pat. No. 5,594,157, issued on Jan. 14, 1997 in the name of Abbott Laboratories and U.S. Pat. No. 5,530,020 issued on Jun. 25, 1996 in the name of Abbott Laboratories each provided deoxygenated taxol compounds which were prepared from a natural product, 9-dihydro-13-acetylbaccatin III, which was isolated from *Taxus canadensis*, as well as analogs of taxol which were prepared therefrom.

U.S. Pat. No. 5,440,056, issued on Aug. 8, 1995 in the name of Abbott Laboratories, provided deoxygenated taxol products prepared from a natural product, 9-dihydro-13-acetylbaccatin III, which is isolated from *Taxus canadensis*.

U.S. Pat. No. 4,924,011, re-issued as U.S. Pat. No. 34,277 in the name of Denis et al provided the first successful semi-synthesis of paclitaxel using the starting material 10-deacetylbaccatin III which can be extracted in relatively high yield from the needles of *Taxus baccata* species.

It would be highly desirable to be provided with a novel semi-synthetic process for the preparation of paclitaxel, docetaxel, the anticancer drugs, and 10-deacetylbaccatin III, a useful precursor for making them, the most popular anticancer drugs, and other taxane compounds.

SUMMARY OF THE INVENTION

In accordance with the present invention there is provided a novel semi-synthetic process for the preparation of paclitaxel, docetaxel, the anticancer drugs, and 10-deacetylbaccatin III, a useful precursor for making paclitaxel and docetaxel, the most popular anticancer drugs, and other taxane compounds It is also desirable to provide a semi-synthesis process for 10-deacetylbaccatin III.

It is also desirable provide a semi-synthetic process for the preparation of paclitaxel, docataxel and 10-deacetylbaccatin III from 9-dihydro-13-acetylbaccatin III.

A need still exists for an efficient process for converting 9-dihydro-13 acetylbaccatin III to 10-deacetylbaccatin III (DAB III).

In accordance with the present invention there is provided a compound of formula (I), (II), (III) or (IV):

(I)

(II)

(III)

(IV)

wherein

R₁ is a hydrogen atom or a suitable protecting group for a hydroxyl group;

R₂ is a hydrogen atom or a suitable protecting group for a hydroxyl group;

R₃ is a hydrogen atom or a suitable protecting group for a hydroxyl group; and

R is a hydrogen atom, a $C_1$-$C_{20}$ alkyl linear or branched, $C_1$-$C_{20}$ acyl group, $C_1$-$C_{20}$ halogenated acyl group, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_1$-$C_{20}$ alkyloxy $C_6$-$C_{20}$ alkylaryl, $C_1$-$C_{12}$ heteroaryl, $C_2$-$C_{20}$ alkylheterocyclyl, or $C_2$-$C_{20}$ alkylheteroaryl, said alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of said substituent(s) being chosen from F, Cl, Br, I, OH, SH, $NH_2$, $NO_2$, CN, $CF_3$, —SH, —OCH₂Ph, —OPh, —SCH₃, —SPh, —SCH₂Ph, —COOH, —COOR₆ in which R₆ is a $C_1$-$C_6$ alkyl, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, or $C_2$-$C_{20}$ alkylheteroaryl.

In accordance with the present invention, suitable protecting group for a hydroxyl group is chosen from $C_1$-$C_{25}$ ethers, $C_1$-$C_{25}$ substituted methyl ethers, $C_1$-$C_{25}$ substituted ethyl ethers, $C_1$-$C_{25}$ acyl groups, $C_1$-$C_{25}$ halogenated acyl groups, $C_1$-$C_{25}$ substituted benzyl ethers, $C_1$-$C_{25}$ silyl ethers, $C_1$-$C_{25}$ esters, $C_1$-$C_{25}$ carbonates, and $C_1$-$C_{25}$ sulfonates.

In accordance with the present invention, suitable protecting group for a hydroxyl group is chosen from methyl, methoxymethyl, benzyloxymethyl, tetrahydropyranyl, tetrahydrofuranyl, 2-(trimethylsilyl)ethoxymethyl, dioxanyl, 1-ethoxyethyl, 1-(2-chloroethoxy)ethyl, 2,2,2-trichloroethyl, t-butyl, allyl, propargyl, benzyl, p-methoxybenzyl, diphenylmethyl, triphenylmethyl, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl, benzylformate, methylcarbonyl, ethylcarbonyl, methoxymethylarbonyl, trichloroethoxycarbonyl, benzylcarbonyl, benzyloxycarbonyl. allylsulfonyl, methanesulfonyl, and p-toluenesulfonyl.

In accordance with the present invention, in a preferred compound R₁ is triethylsilyl.

In accordance with the present invention, in a preferred compound R₂ is acetyl.

In accordance with the present invention, in a preferred compound R₃ is ethoxyethyl.

In accordance with the present invention, in a preferred compound R₄ is a $C_1$-$C_6$ alkyl, phenyl, t-butyloxyl, a $C_2$-$C_6$ alkenyl, tetrahydrofuranyl, or tetrahydropyranyl.

In accordance with the present invention, in a preferred compound R₄ is a pentyl, phenyl, t-butyloxyl, but-2-enyl, tetrahydrofuranyl, or tetrahydropyranyl.

In accordance with the present invention, there is provided a compound of formula (V) or (VI):

(V)

(VI)

wherein

R₁ is a hydrogen atom or a suitable protecting group for a hydroxyl group;

R₂ is a hydrogen atom or a suitable protecting group for a hydroxyl group;

R₃ is a hydrogen atom or a suitable protecting group for a hydroxyl group; and

R₄ is a hydrogen atom, a $C_1$-$C_{20}$ alkyl linear or branched, $C_1$-$C_{20}$ acyl group, $C_1$-$C_{20}$ halogenated acyl group, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_1$-$C_{20}$ alkyloxy $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group; and R₅ is a hydrogen atom or a suitable protecting group for a hydroxyl group, said alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of said substituent(s) being chosen from F, Cl, Br, I, OH, SH, $NH_2$, $NO_2$, CN, $CF_3$, —SH, —OCH₂Ph, —OPh, —SCH₃, —SPh, —SCH₂Ph, —COOH, —COOR₆ in which R₆ is a $C_1$-$C_6$ alkyl, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, or $C_2$-$C_{20}$ alkylheteroaryl.

In accordance with the present invention, in a preferred compound the suitable protecting group for a hydroxyl group is chosen from $C_1$-$C_{25}$ ethers, $C_1$-$C_{25}$ substituted methyl ethers, $C_1$-$C_{25}$ substituted ethyl ethers, $C_1$-$C_{25}$ acyl groups, $C_1$-$C_{25}$ halogenated acyl groups, $C_1$-$C_{25}$ substituted benzyl ethers, $C_1$-$C_{25}$ silyl ethers, $C_1$-$C_{25}$ esters, $C_1$-$C_{25}$ carbonates, and $C_1$-$C_{25}$ sulfonates.

In accordance with the present invention, in a preferred compound the suitable protecting group for a hydroxyl group is chosen from methyl, methoxymethyl, benzyloxymethyl, tetrahydropyranyl, tetrahydrofuranyl, 2-(trimethylsilyl)ethoxymethyl, dioxanyl, 1-ethoxyethyl, 1-(2-chloroethoxy)ethyl, 2,2,2-trichloroethyl, t-butyl, allyl, propargyl, benzyl, p-methoxybenzyl, diphenylmethyl, triphenylmethyl, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl, benzylformate, methylcarbonyl, ethylcarbonyl, methoxymethyl arbonyl, trichloroethoxycarbonyl, benzylcarbonyl, benzyloxycarbonyl. allylsulfonyl, methanesulfonyl, and p-toluenesulfonyl.

In accordance with the present invention, in a preferred compound $R_1$ is triethylsilyl.

In accordance with the present invention, in a preferred compound $R_2$ is acetyl.

In accordance with the present invention, in a preferred compound $R_3$ is ethoxyethyl.

In accordance with the present invention, in a preferred compound $R_4$ is a $C_1$-$C_6$ alkyl, phenyl, t-butyloxyl, a $C_2$-$C_6$ alkenyl, tetrahydrofuranyl, or tetrahydropyranyl.

In accordance with the present invention, in a preferred compound $R_4$ is a pentyl, phenyl, t-butyloxyl, but-2-enyl, tetrahydrofuranyl, or tetrahydropyranyl.

In accordance with the present invention, in a preferred compound $R_5$ is triethylsilyl.

In accordance with the present invention, there is provided a process for preparing a compound of formula (II):

(II)

said process comprising reacting an oxidizing agent with a compound of formula (I):

(I)

wherein $R_1$ is a hydrogen atom or a suitable protecting group for a hydroxyl group; and $R_2$ is a hydrogen atom or a suitable protecting group for a hydroxyl group.

In accordance with the present invention, the suitable protecting group for a hydroxyl group is chosen from $C_1$-$C_{25}$ ethers, $C_1$-$C_{25}$ substituted methyl ethers, $C_1$-$C_{25}$ substituted ethyl ethers, $C_1$-$C_{25}$ acyl groups, $C_1$-$C_{25}$ halogenated acyl groups, $C_1$-$C_{25}$ substituted benzyl ethers, $C_1$-$C_{25}$ silyl ethers, $C_1$-$C_{25}$ esters, $C_1$-$C_{25}$ carbonates, and $C_1$-$C_{25}$ sulfonates.

In accordance with the present invention, the suitable protecting group for a hydroxyl group is chosen from methyl, methoxymethyl, benzyloxymethyl, tetrahydropyranyl, tetrahydrofuranyl, 2-(trimethylsilyl)ethoxymethyl, dioxanyl, 1-ethoxyethyl, 1-(2-chloroethoxy)ethyl, 2,2,2-trichloroethyl, t-butyl, allyl, propargyl, benzyl, p-methoxybenzyl, diphenylmethyl, triphenylmethyl, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl, benzylformate, methylcarbonyl, ethylcarbonyl, methoxymethyl arbonyl, trichloroethoxycarbonyl, benzylcarbonyl, benzyloxycarbonyl. allylsulfonyl, methanesulfonyl, and p-toluenesulfonyl.

In accordance with the present invention, $R_1$ is triethylsilyl.

In accordance with the present invention, $R_2$ is acetyl.

In accordance with a process of the present invention, the oxidizing agent is chosen from tetra-n-propylammonium perruthenate, Collin's reagent, Swern reagent [$(COCl)_2$, DMSO, $Et_3N$], acidic pyridinium chlorochromate (PCC), pyridinium dichromate (PDC), $CrO_2$, and John's reagent.

In accordance with the present invention, there is provided a process for converting 9-dihydro-13-acetylbaccatin III into a taxane derivative comprising the step of removing 10-acetyl group and oxidizing the C-9 and C-10 positions of the 9-dihydro-13-acetylbaccatin III.

In accordance with the present invention, the oxidizing step is achieved by the addition of an oxidizing agent chosen from tetra-n-propylammonium perruthenate, Collin's reagent, Swern reagent, PCC, PDC, $CrO_2$ and John's reagent.

In accordance with the present invention, there is provided a process for preparing paclitaxel, docetaxel and a derivative thereof comprising the steps of:

(a) protecting the C-7 hydroxy group of 9-dihydro-13-acetylbaccatin III with a suitable protecting group to obtain a protected product;

(b) deacetylating the 10-acetyl group of the protected product; and (c) oxidizing the C-9 and C-10 hydroxyl group of the protected product.

In accordance with a process of the present invention, the protecting group is chosen from benzyl, $C_1$-$C_{25}$ substituted benzyl, benzylformate, $C_1$-$C_{25}$ substituted benzylformate, tosyl, substituted tosyl, dihydropyranyl, methoxymethyl, benzoyl, $C_1$-$C_{25}$ substituted benzoyl, $C_1$-$C_{25}$ trialkylsilyl, 2-(trimethylsilyl)ethoxymethyl, benzyloxycarbonyl, In accordance with a process of the present invention, the oxidizing step is achieved by the addition of an oxidizing reagent chosen from of tetra-n-propylammonium perruthenate, Collin's reagent, Swern reagent, PCC, PDC, $CrO_2$ and John' reagent.

In accordance with a process of the present invention, it further comprises the step of deacetylating the C-13 position.

In accordance with a process of the present invention, it further comprises the step of reducing the C-10 ketone into C-10 hydroxyl group.

In accordance with the present invention, there is provided a process for preparing a compound of formula 8:

comprising the step of reducing the C-10 ketone of a compound of formula 7:

In accordance with a process of the present invention, it further comprises the step of deprotecting the C-7 position to obtain 10-deacetylbaccatin III.

In accordance with a process of the present invention, it further comprises the steps of adding a suitable side chain to the C-13 position, reducing C-10 and selectively deprotecting to obtain a desired product.

In accordance with a process of the present invention, the deprotection is done at the C-7 and 2' positions to obtain paclitaxel and docetaxel.

In accordance with a process of the present invention, the side chain is chosen from (2R,3S)—N-benzoyl-O-(1-ethoxy-ethyl)-3-phenylisoserine; (3R,4S)-3-(1-ethoxyethoxy)-4-(phenyl)-N-benzoyl-2-azetidinone; (2R,3S)—N-boc-O-(1-ethoxyethyl)-3-phenylisoserine and (3R,4S)-3-(1-ethoxyethoxy)-4-(phenyl)-N-boc-2-azetidinone.

In accordance with a process of the present invention, the taxane derivative is paclitaxel or docetaxel.

DETAILED DESCRIPTION OF THE INVENTION

The present invention concerns 9,10-diketo taxane derivatives formed in chemical conversion from 9-dihydro-13-acetylbaccatin III (9-DHAB) for the efficient production of paclitaxel and docetaxel analogs and their intermediate. Such conversion processes may include protection of 7-OH of the 9-DHAB, deacelaytion of C-10 position, and oxidation of C-9, and C-10 hydroxyl groups to yield a intermediate compound 7-triethylsilyl-9,10-diketo-13-acetylbaccatin III (6). These process also may include the attachment of the paclitaxel and docetaxel side chai to the 9,10-diketo moiety (compound 7), which allows for the synthesis of paclitaxel, docetaxel and their analogs as well as their intermediates with variable C-13 side chain structure.

A first broad aspect of the present invention provides a novel process for making paclitaxel and docetaxel by using a novel precursor, 9-dihydro-13-acetylbaccatin III, which is abundant in *Taxus canadensis*, the species commonly found in Eastern Canada and Northeast United States. The isolation yield for this compound is 0.1-0.2%.

A second broad aspect of the present invention provides a novel synthetic route in a process for the conversion of 9-dihydro-13-acetylbaccatin III to paclitaxel and docetaxel, the process comprising the two steps of firstly, reacting a protected paclitaxel or docetaxel side chain precursor with 7-O-triethylsilyl-9,10-diketobaccatin III (7), thereby to produce 7-O-triethylsilyl-9,10-diketodocetaxel (12), and 7-O-triethylsilyl-9,10-diketopaclitaxel (1) containing a protected side chain. The second step of reducing the C-10 keto of the intermediates 12 and 14, to yield intermediates 7-O-triethylsilyl-2'-EE-docetaxel 13 and 7-O-triethylsilyl-2'-EE-10-deacetylpaclitaxel (15), and final step of removing the protecting groups from 7-O-triethylsilyl-2'-EE-docetaxel, or acetylating C-10 hydroxyl then removing protection groups from 7-O-triethylsilyl-2'-EE-10-deacetylpaclitaxel, to yield the designed products, docetaxel or paclitaxel.

A third broad aspect of the present invention provides a process for the conversion of 9-dihydro-13-acetylbaccatin III to 10-deacetylbaccatin III, comprising the sequential steps of converting 7-O-triethylsilyl-9,10-diketo-13-acetylbaccatin III to 7-O-triethylsilyl-9,10-diketo-1baccatin III, reducing said 7-O-triethylsilyl-9,10-diketobaccatin III to 7-O-triethylsilyl-10-deacetylbaccatin III, removing the 7-O-triethylsilyl protecting group to yield 10-deacetylbaccatin III.

A fourth broad aspect of the present invention provides a novel process for the conversion of 9-dihydro-13-acetylbaccatin III paclitaxel and docetaxel which comprises the sequential steps of: effecting a triethylsilylation reaction on the 7-hydroxy group of 9-dihydro-13-acetylbaccatin III while substantially-simultaneously deacetylating the 10-acetyl group to yield a 10-hydroxy group, thereby to produce 7-O-triethylsilyl-10-deacetyl-9-dihydro-13-acetylbaccatin III (D; oxidizing the 9-, and 10-hydroxyl group of compound 5 to produce 13-acetyl-9,10-diketo-7-triethylsilylbaccatin III 6, removing the 13-acetyl group of 7-O-triethylsilyl-9,10-diketo-13-acetylbaccatin III thereby to produce 7-O-triethylsilyl-9,10-diketobaccatin III 7; attaching a paclitaxel or docetaxel side chain precursor to the intermediate 7, thereby to produce 7-triethylsilyl-9,10-diketo-10-deacetylpaclitaxel 14 or 7-triethylsilyl-9,10-diketodocetaxel 12, reducing the 10-keto group on the intermediates 12 and 14, thereby to produce 7-O-triethylsilyl-2'-EE-docetaxel and 7-O-triethylsilyl-2'-EE-10-deacetylpaclitaxel; acetylating the C-10 hydroxy of intermediate 14 to yield compound 18, then deprotection on intermediates 12 and 18 to produce docetaxel and paclitaxel.

The suitable protecting groups for hydroxyl groups can be any protecting group that would be used by a person skilled in the art.

Such protecting groups can be those described in Theodora W. Greene et al., Protective Groups in Organic Synthesis, Third Edition, John Wiley & Sons, Inc., 1999, pp. 17-21, which is hereby incorporated by reference.

The protecting groups for hydroxyl groups can be, for example, ethers (such as methyl), or substituted methyl ethers (such as methoxymethyl; methylthiomethyl; (phenyldimethylsilyl)methoxymethyl; benzyloxymethyl; ρ-methoxybenzyloxymethyl; ρ-nitrobenzyloxymethyl; o-nitrobenzyloxymethyl; (4-methoxyphenoxy)methyl; guaiacolmethyl; t-butoxymethyl; 4-pentenyloxymethyl; siloxymethyl; 2-methoxyethoxymethyl; 2,2,2-trichloroethoxymethyl; bis (2-chloroethoxy)methyl; 2-(trimethylsilyl)ethoxymethyl; methoxymethyl; tetrahydropyranyl; 3-bromotetrahydropyranyl; tetrahydrothiopyranyl; 1-methoxycyclohexyl; 4-methoxytetrahydropyranyl; 4-methoxytetrahydrothiopyranyl; 4-methoxytetrahydrothiopyranyl s,s-dioxide; 1-[(2-chloro-4-methyl)phenyl]-4-methoxypiperidin-4-yl; 1-(2-fluorophenyl)-4-methoxypiperidin-4-yl; 1,4-dioxan-2-yl; tetrahydrofuranyl; tetrahydrothiofuranyl; 2,3,3a,4,5,6,7,7a-octahydro-7,8,8-trimethyl-4,7-methanobenzofuran-2-yl).

The protecting groups for hydroxyl groups can be, for example, substituted ethyl ethers (such as 1-ethoxyethyl; 1-(2-chloroethoxy)ethyl; 1-[2-(trimethylsilyl)ethoxy]ethyl; 1-methyl-1-methoxyethyl; 1-methyl-1-benzyloxyethyl; 1-methyl-1-benzyloxy-2-fluoroethyl; 1-methyl-1-phenoxyethyl; 2,2,2-trichloroethyl; 1,1-dianisyl-2,2,2-trichloroethyl; 1,1,1,3,3,3-hexafluoro-2-phenylisopropyl; 2-trimethylsilylethyl; 2-(benzylthio)ethyl; 2-(phenylselenyl)ethyl; t-butyl; allyl; propargy; ρ-chlorophenyl; ρ-methoxyphenyl; ρ-nitrophenyl; 2,4-dinitrophenyl; 2,3,5,6-tetrafluoro-4-(trifluoromethyl)phenyl; benzyl), substituted benzyl ethers (such as ρ-methoxybenzyl; 3,4-dimethoxybenzyl; o-nitrobenzyl; ρ-nitrobenzyl; ρ-halobenzyl; 2,6-dichlorobenzyl; ρ-cyanobenzyl; ρ-phenylbenzyl; 2,6-difluorobenzyl; ρ-acylaminobenzyl; ρ-azidobenzyl; 4-azido-3-chlorobenzyl; 2-trifluoromethylbenzyl; ρ-(methylsulfinyl)benzyl; 2- and 4-picolyl; 3-methyl-2-picolyl n-oxide; 2-quinolinylmethyl; 1-pyrenylmethyl; diphenylmethyl; p,p'-dinitrobenzhydryl; 5-dibenzosuberyl; triphenylmethyl; α-naphthyldiphenylmethyl; ρ-methoxyphenyldiphenylmethyl; di(ρ-methoxyphenyl) phenylmethyl; tri(ρ-methoxyphenyl)methyl; 4-(4'-bromophenacyloxy)phenyldiphenylmethyl; 4,4',4"-tris(4,5-dichlorophthalimidophenyl)methyl; 4,4',4"-tris (levulinoyloxyphenyl)methyl; 4,4',4"-tris (benzoyloxyphenyl)methyl; 4,4'-dimethoxy-3"-[n-(imidazolylmethyl)]trityl; 4,4'-dimethoxy-3"-[n-(imidazolylethyl)carbamoyl]trityl; 1,1-bis(4-methoxyphenyl)-1'-pyrenylmethyl; 4-(17-tetrabenzo[a,c,g,i] fluorenylmethyl)-4,4"-dimethoxytrityl; 9-anthryl; 9-(9-phenyl)xanthenyl; 9-(9-phenyl-10-oxo)anthryl; 1,3-benzodithiolan-2-yl; benzisothiazolyl s,s-dioxido) silyl ethers (such as trimethylsilyl; triethylsilyl; triisopropylsilyl; dimethylisopropylsilyl; diethylisopropylsilyl; dimethylthexylsilyl; t-butyldimethylsilyl; t-butyldiphenylsilyl; tribenzylsilyl; tri-ρ-xylylsilyl; triphenylsilyl; diphenylmethylsilyl; di-t-butylmethylsilyl; tris(trimethylsilyl)silyl: sisyl; (2-hydroxystyryl)dimethylsilyl; (2-hydroxystyryl)diisopropylsilyl; t-butylmethoxyphenylsilyl; t-butoxydiphenylsilyl), esters (such as formate; benzoylformate; acetate; chloroacetate; dichloroacetate; trichloroacetate; trifluoroacetate; methoxyacetate; triphenylmethoxyacetate; phenoxyacetate; ρ-chlorophenoxyacetate; phenylacetate; ρ-p-phenylacetate; diphenylacetate; nicotinate; 3-phenylpropionate; 4-pentenoate; 4-oxopentanoate (levulinate); 4,4-(ethylenedithio) pentanoate; 5-[3-bis(4-methoxyphenyl)hydroxymethylphenoxy]levulinate; pivaloate; 1-adamantoate; crotonate; 4-methoxycrotonate; benzoate; ρ-phenylbenzoate; 2,4,6-trimethylbenzoate (mesitoate), carbonates (such as methylcarbonyl; methoxymethylcarbonyl; 9-fluorenylmethylcarbonyl; ethylcarbonyl; 2,2,2-trichloroethylcarbonyl; 1,1-dimethyl-2, 2,2-trichloroethylcarbonyl; 2-(trimethylsilyl)ethylcarbonyl; 2-(phenylsulfonyl)ethylcarbonyl; 2-(triphenylphosphonio) ethylcarbonyl; isobutylcarbonyl; vinylcarbonyl; allylcarbonyl; ρ-nitrophenylcarbonyl; benzylcarbonyl; ρ-methoxybenzylcarbonyl; 3,4-dimethoxybenzylcarbonyl; o-nitrobenzylcarbonyl; ρ-nitrobenzylcarbonyl), carbonates cleaved by b-elimination (such as 2-dansylethyl; 2-(4-nitrophenyl)ethyl; 2-(2,4-dinitrophenyl)ethyl; 2-cyano-1-phenylethyl; s-benzyl thiocarbonate; 4-ethoxy-1-naphthyl; methyl dithiocarbonate), miscellaneous esters (such as 2,6-dichloro-4-methylphenoxyacetate; 2,6-dichloro-4-(1,1,3,3-tetramethylbutyl)phenoxyacetate; 2,4-bis(1,1-dimethylpropyl)phenoxyacetate; chlorodiphenylacetate; isobutyrate; monosuccinoate; (e)-2-methyl-2-butenoate (tigloate); o-(methoxycarbonyl)benzoate; ρ-p-benzoate; α-naphthoate; nitrate; alkyl n,n,n',n'-tetramethylphosphorodiamidate; 2-chlorobenzoate; 4-bromobenzoate; 4-nitrobenzoate; 3'5'-dimethoxybenzoin; n-phenylcarbamate; borate; dimethylphosphinothioyl; 2,4-dinitrophenylsulfenate), and sulfonate (such as sulfate; allylsulfonate; methanesulfonate (mesylate); benzylsulfonate; tosylate; 2-[(4-nitrophenyl) ethyl]sulfonate).

The present invention will be more readily understood by referring to the following examples which are given to illustrate the invention rather than to limit its scope.

Example 1

Preparation of
7-TES-10-Deacetyl-9-Dihydro-13-Acetylbaccatin III
(5)

Figure 1:
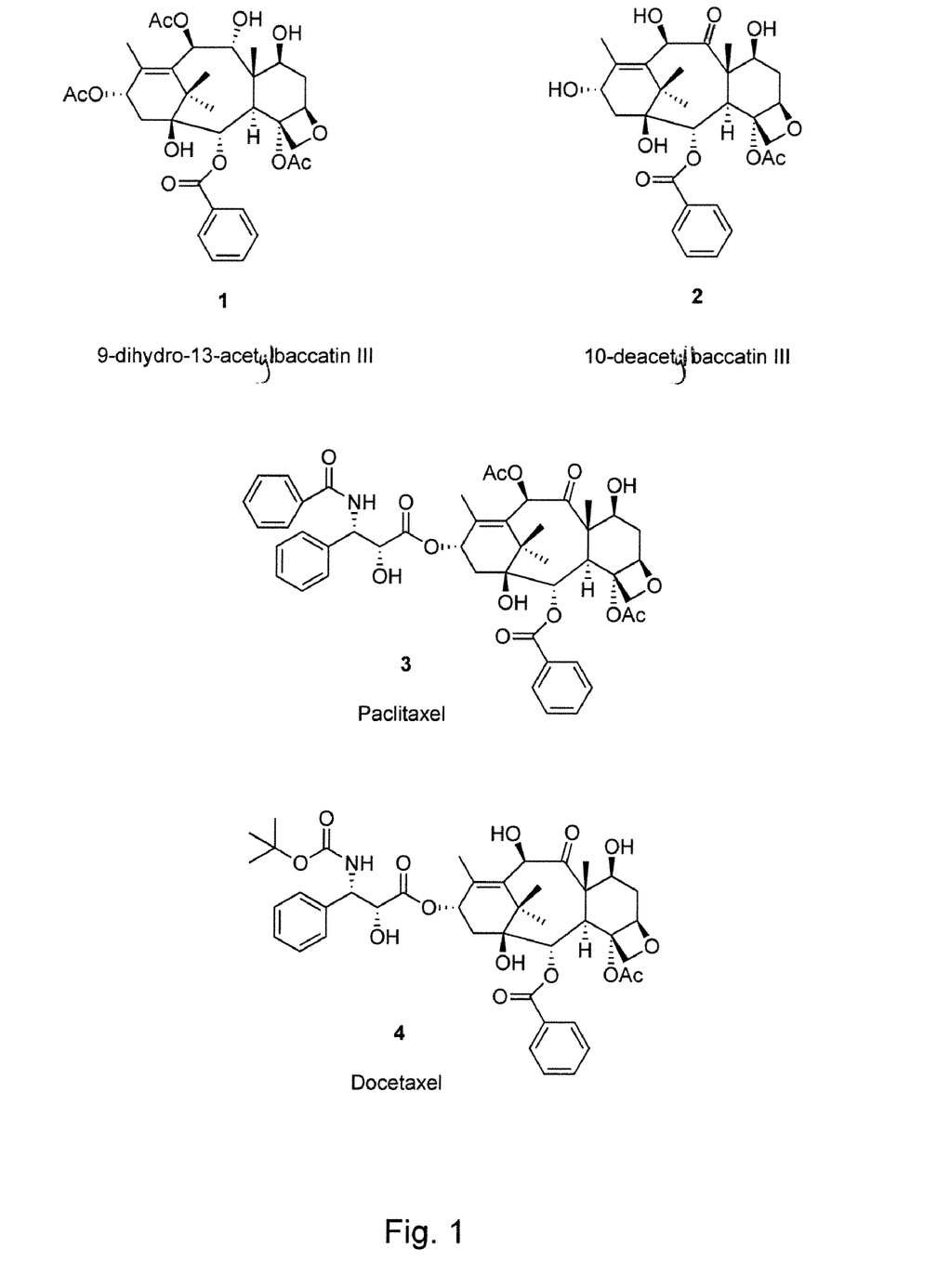
FIG. 1 illustrates taxane derivatives.

To 10 ml of acetonitrile, 102 mg of 9-dihydro-13-acetylbaccatin III (shown in FIG. 1 as compound 1) and 73 mg of n-tetrabutylammonium iodide were added, the mixture was stirred for 5 minutes until 9-dihydro-13-acetylbaccatin III was completely dissolved. The mixture was kept in −10° C., then chlorotriethylsilane was added dropwise. The mixture was stirred for another 5-10 minutes at −10° C. before 26 mg of sodium methoxide was poured into the round bottom flask. This mixture was kept stirred for another one hour at the same temperature then the temperature was raised to 0° C., and maintained at 0° C. for about 1 hour. Then the temperature was raised to room temperature the mixture was kept stirred for 2 more hours. The reaction was quenched by dilution with brine, and extracted with ethyl acetate for three times. The organic phase was combined and evaporated to dryness in vacuum. The residue was purified by preparative TLC to yield 7-O-triethylsilyl-10-deacetyl-9-dihydro-13-acetylbaccatin III (shown in FIG. 2 as compound 5) as a white solid (85 mg, 85%).

Example 2

Preparation of
7-TES-9,10-Diketo-13-Acetylbaccatin III (6)

Figure 2:
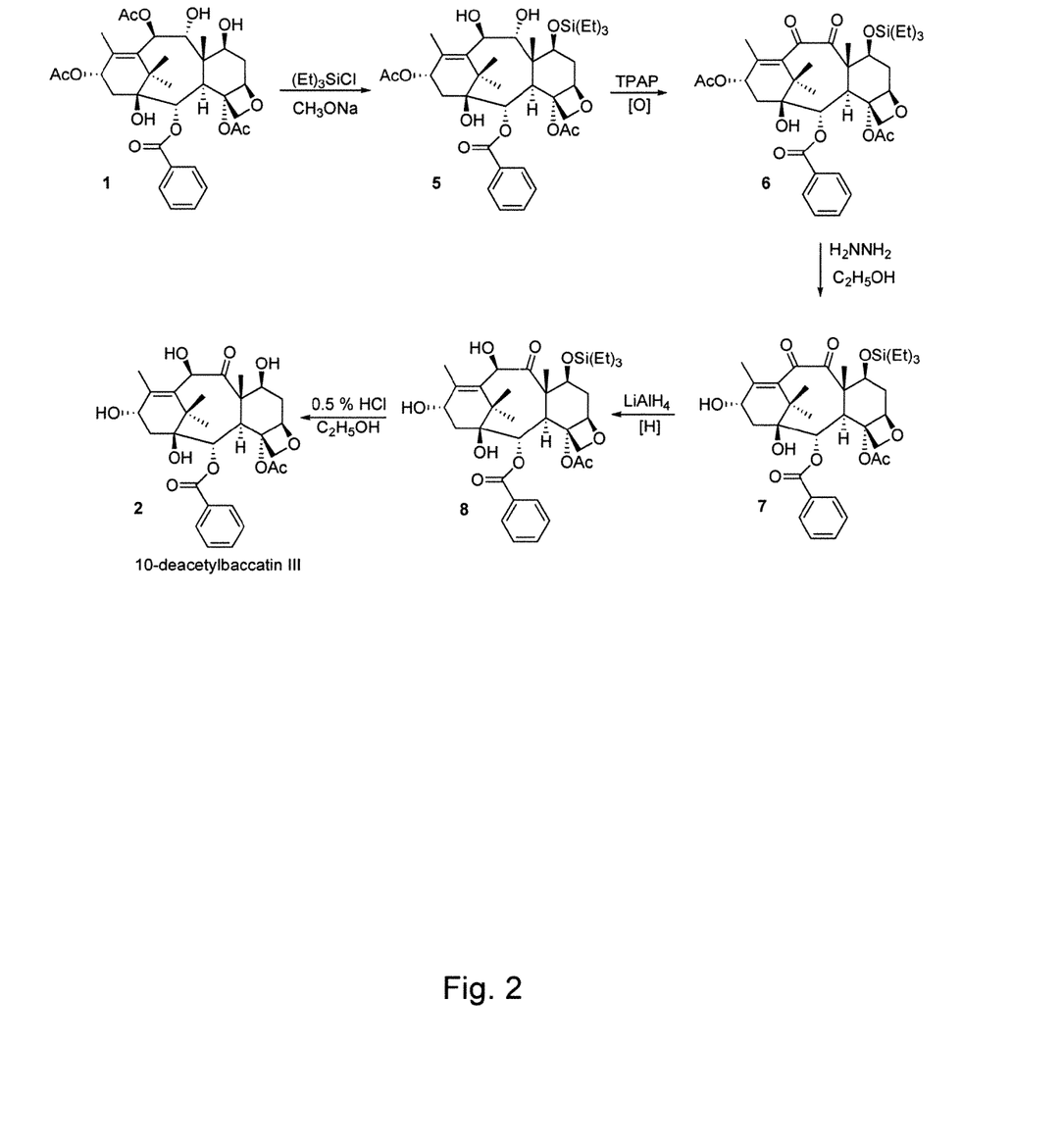
FIG. 2 illustrates the reaction scheme 1 for preparing compound 2.
Figure 3:
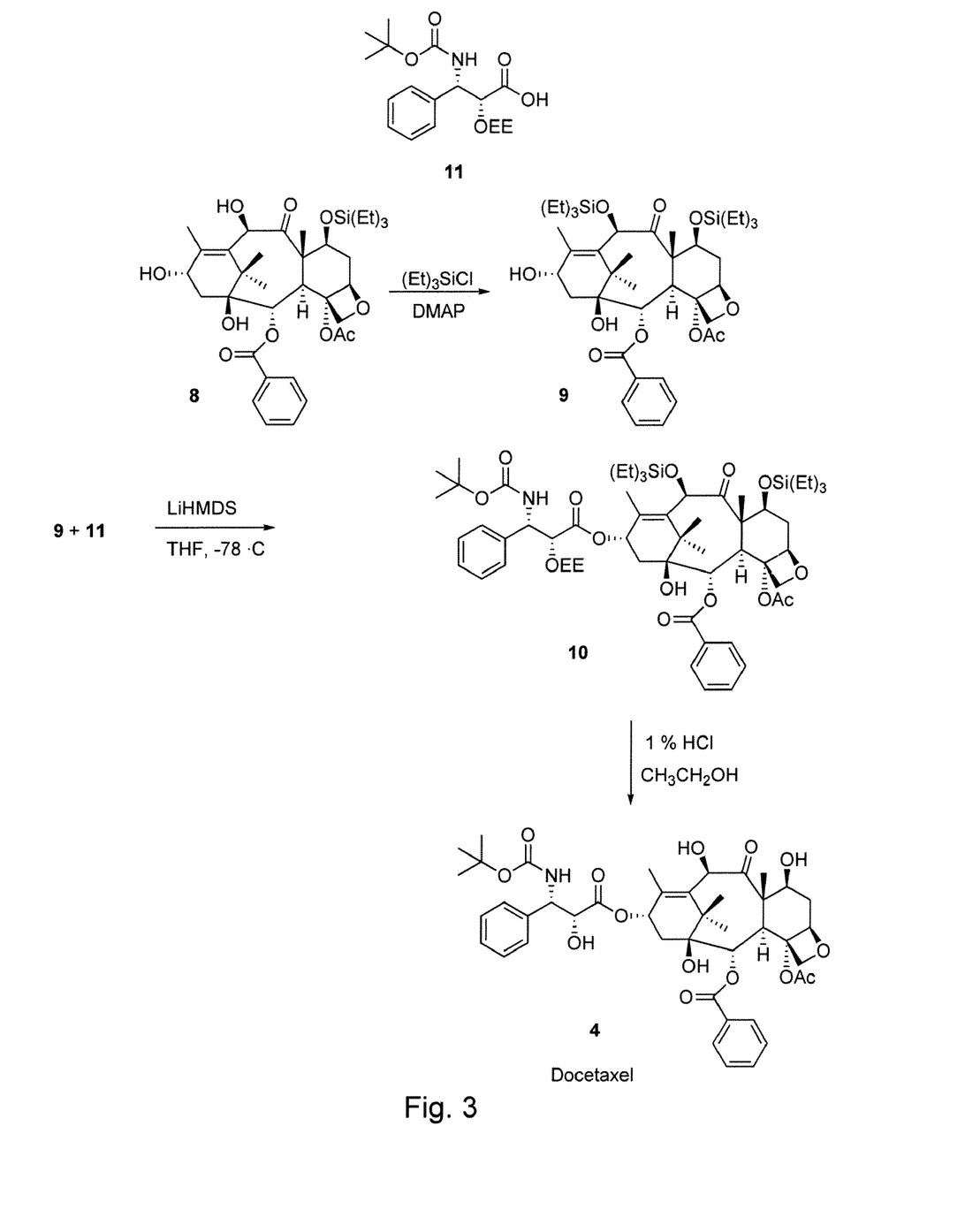
FIG. 3 illustrates the reaction scheme 2 for preparing compound 4.

73 mg of 7-TES-10-deacetyl-9-dihydro-13-acetylbaccatin III (shown in FIG. 2 as compound 5) and 35 mg of 4-methylmorpholine-N-oxide (NMO) were added into a round bottom flask, and 10 ml of acetonitrile/acetone (3:1) mixture was added. Then a molecular sieve was added to the mixture which stirred for 5 minutes, 10 mg of tetra-n-propylammonium perruthenate (TPAP) was then added, and the mixture was stirred for about 6 hours at room temperature, following which the temperature was raised to 40° C. The mixture was maintained at that temperature overnight until the reaction was completed. Once the reaction was completed, the mixture was poured into a short silica gel column. The column was eluted with 50 ml of dichloromethane ($CH_2Cl_2$) to give a $CH_2C_{12}$ fraction, which was concentrated to dryness. The residue was purified by preparative TLC to yield 65 mg white solid which identified as 7-TES-9,10-diketo-13-acetylbaccatin III as shown in FIG. 2 as compound 6.

Example 3

Preparation of 10-Deacetylbaccatin III (2)

Step A: To a solution of 95% of ethanol, 45 mg of the compound 6 was added and stirred until the solid was completely dissolved, and then hydrazine monohydrate (0.6 ml) was added, then the solution was stirred for 8 hours at room temperature, after that the reaction was quenched by brine and extracted with dichloromethane and organic phase was collected and concentrated to dryness in vacuum. The residue was purified through silica gel column. The product from step A was dissolved in 10 ml of THF, 5 mg of $LiAlH_4$ was then slowly added with stirring. After stirring for 2 hours at room temperature, the reaction was quenched by adding of 1% HCl (0.5 ml) and brine, the product was extracted with $CH_2C_{12}$. The organic phase was concentrated to dryness under vacuum to give final product. Product 7-TES-10-deacetylbaccatin III as shown in FIG. 2 as compound 8 was obtained as slightly yellow crystals.

Step B: 7-TES-10-deacetylbaccatin III was dissolved in a mixture of acetonitrile and acetone (3:1), the solution then was stirred at room temperature for a few minutes before 5 ml of sodium hypochloride (NaOCl) was added dropwise. The mixture was reacted at room temperature for 2 hours and then quenched with brine and extracted with ethyl acetate. The ethyl acetate phase was concentrated to dryness and the residue was re-crystallized from acetonitrile to yield 10-deacetylbaccatin III as a white powder (shown as compound 2).

Example 4

Preparation of 7-TES-9,10-Diketodocetaxel (12)

Figure 4:
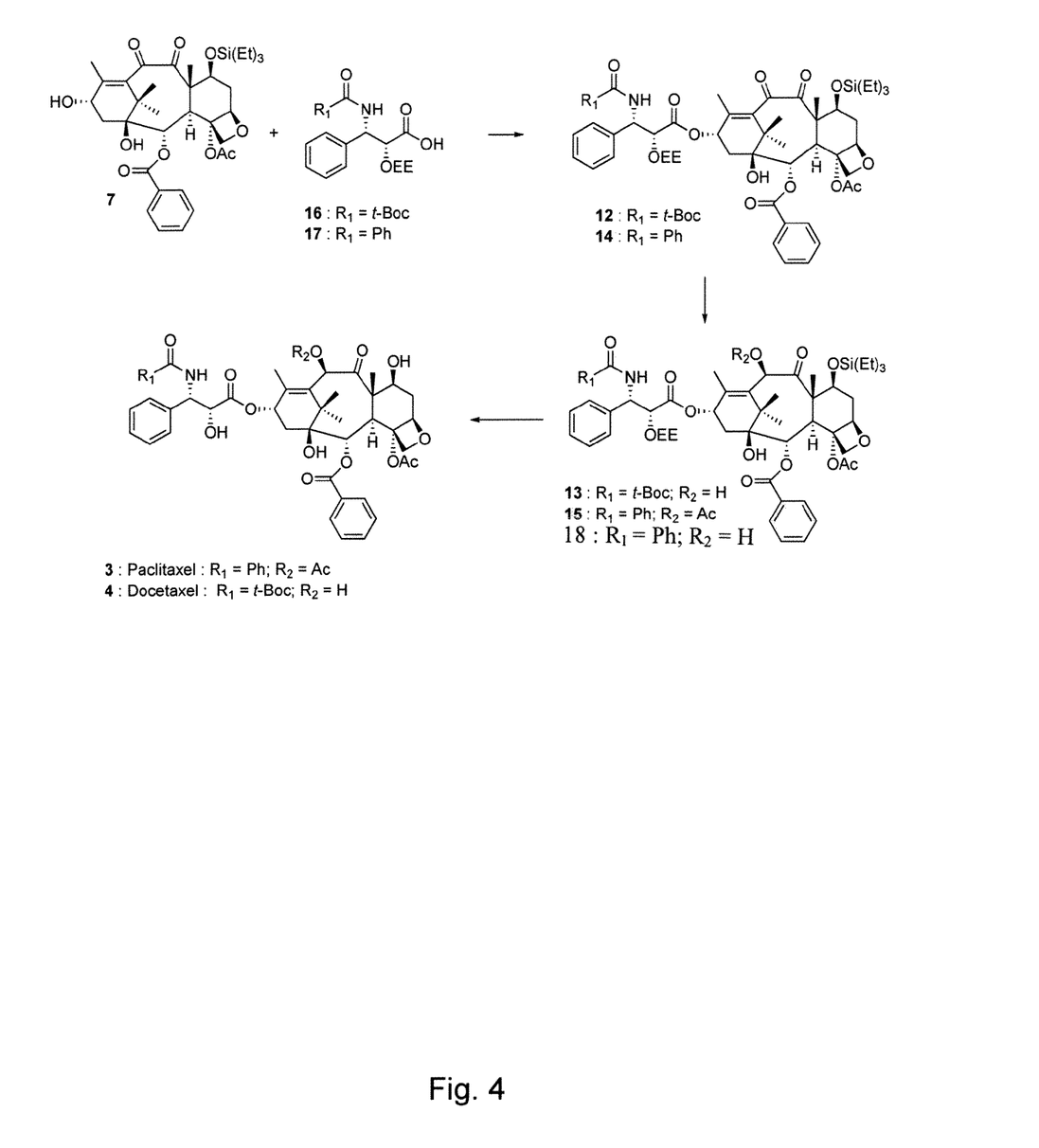
FIG. 4 illustrates the reaction scheme 3 for preparing compounds 3 and 4.

Step A: To a solution of 95% ethanol, 40 mg of compound 6 was added and stirred for a few minutes until the solid was dissolved, then 1 ml of hydrazine monohydrate was added. The mixture was stirred at room temperature for 8 hours, then diluted with ethyl acetate (50 ml) and poured into saturated $NH_4Cl$ solution (40 ml). The organic layer was separated and concentrated. The residue was purified by preparative TLC to give 30 mg of 7-TES-9,10-diketobaccatin III (see compound 7 on FIG. 4).

Step B: 35 mg of 7-TES-9,10-diketobaccatin III was placed in a 25 ml round bottom flask, and 3 mole equivalents of protected docetaxel side chain precursor, (2R,3S)—N-boc-O-(1-ethoxyethyl)-3-phenylisoserine or (3R,4S)-3-(1-ethoxyethyl)-4-(phenyl)-N-boc-2-azetidinone, were dissolved in 20 ml of tetrahydrofuran (THF) at −45° C., then 6 mole equivalents of LiHMDS and 1 mole equivalent of $CeCl_3$ were added slowly. The mixture was stirred at −45° C. for 30 minutes then warmed to room temperature. The reaction progress was detected by TLC until completion. Once completed, the mixture was diluted with dichloromethane (50 ml) and poured into saturated $NH_4Cl$ solution (40 ml). The organic layer was separated and concentrated. The residue was purified by preparative TLC to yield 7-TES-9,10-diketodocetaxel (see compound 12 on FIG. 4).

Example 5

Preparation of Docetaxel (4)

Step A: 7-triethylsilyl-2'-EE-docetaxel (13): Compound 12 (1.0 g) was dissolved in THF (30 ml), and the solution was poured into a 50 ml round-bottom flask equipped with a magnetic stirrer, then 0.4 M solution of $CeCl_3.7H_2O$ in THF/MeOH (2/1, 3 ml) was added. The mixture was stirred for 5 minutes at room temperature. $NaBH_4$ (45 mg, 1.2 mmol) was then slowly added with stirring. The mixture was stirred for another 10 minutes at room temperature or until the reaction completed, then the reaction was quenched by adding of 5% HCl (2 ml) and the product 13 was extracted with 50 ml of $CH_2C_{12}$ and saturated $NH_4Cl$ mixture (3:1) The organic layer was separated and evaporated to dryness under reduced pressure, the residue was took to next step without purification (see compound 13 on FIG. 4).

Step B: The residue was re-dissolved in THF, and sodium hypochloride (NaOCl) was added dropwise. The mixture was stirred for 2 hours at room temperature then work-up as above. The residue was purified through flash column chromatography. Docetaxel was obtained as white needles (see compound 4 on FIG. 4).

7-triethylsilyl-2'-EE-10-deacetylpaclitaxel (compound 18) can be made through the same manner as for making intermediate compound 13 by using a paclitaxel side chain attached to 13-C position.

7-triethyl-2'-EE-paclitaxel (15): 1.5 g of 7-triethylsilyl-2'-EE-10-deacetylpaclitaxel (18) was dissolved in THF (20 ml), the solution was poured into a 50 ml round-bottom flask equipped with a magnetic stirrer, then 5 ml of DMAP was added and the mixture was cooled to 0° C., and 5 ml of acetyl chloride was added and the mixture was stirred for 10 hours at 0° C., then the temperature was slowly raised to room temperature and kept for another hour. After the reaction was completed, the reaction was quenched by adding 50 ml of brine. The aqueous solution is extracted twice with ethyl acetate. The combined organic phase are washed with saturated aqueous copper sulphate solution until the DMAP has been completely removed, then with saturated sodium chloride solution and then with water. The organic phase finally dried over anhydrous sodium sulphate, and concentrated to dryness under vacuum. The residue was purified through a silica gel column chromatography to yield 7-triethyl-2'-EE-paclitaxel (15).

After de-protection of 15 by the same manner as to making docetaxel, paclitaxel can be obtained as white powder.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:
1. A compound of formula (I), (II), (III) or (IV):

wherein
$R_1$ is a hydrogen atom or a suitable protecting group for a hydroxyl group;
$R_2$ is a hydrogen atom or a suitable protecting group for a hydroxyl group;
$R_3$ is a hydrogen atom or a suitable protecting group for a hydroxyl group;
and
$R_4$ is a hydrogen atom, a $C_1$-$C_{20}$ alkyl linear or branched, $C_1$-$C_{20}$ acyl group, $C_1$-$C_{20}$ halogenated acyl group, $C_3$-$C_{12}$ cycloalkyl, $C_2$-$C_{20}$ alkenyl, $C_2$-$C_{20}$ alkynyl, $C_6$-$C_{12}$ aryl, $C_6$-$C_{20}$ aralkyl, $C_1$-$C_{20}$ alkyloxy $C_6$-$C_{20}$ alkylaryl, said alkyl, cycloalkyl, alkenyl, alkynyl, aryl, aralkyl, alkylaryl, are unsubstituted or substituted with at least one substituent, each of said substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_6$ in which $R_6$ is a $C_1$-$C_6$ alkyl, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{20}$ hydroxyalkyl, $C_6$-$C_{12}$ hydroxyaryl.

2. The compound of claim 1, wherein said suitable protecting group for a hydroxyl group is chosen from $C_1$-$C_{25}$ ethers, $C_1$-$C_{25}$ substituted methyl ethers, $C_1$-$C_{25}$ substituted ethyl ethers, $C_1$-$C_{25}$ acyl groups, $C_1$-$C_{25}$ halogenated acyl groups, $C_1$-$C_{25}$ substituted benzyl ethers, $C_1$-$C_{25}$ silyl ethers, $C_1$-$C_{25}$ esters, $C_1$-$C_{25}$ carbonates, and $C_1$-$C_{25}$ sulfonates.

3. The compound of claim 1, wherein said suitable protecting group for a hydroxyl group is chosen from methyl, methoxymethyl, benzyloxymethyl, tetrahydropyranyl, tetrahydrofuranyl, 2-(trimethylsilyl)ethoxymethyl, dioxanyl, 1-ethoxyethyl, 1-(2-chloroethoxy)ethyl, 2,2,2-trichloroethyl, t-butyl, allyl, propargyl, benzyl, p-methoxybenzyl, diphenylmethyl, triphenylmethyl, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl, benzylformate, methylcarbonyl, ethylcarbonyl, methoxymethylarbonyl, trichloroethoxycarbonyl, benzylcarbonyl, benzyloxycarbonyl, allylsulfonyl, methanesulfonyl, and p-toluenesulfonyl.

4. The compound of claim 1, wherein $R_1$ is triethylsilyl.

5. The compound of claim 1, wherein $R_2$ is acetyl.

6. The compound of claim 1, wherein $R_3$ is ethoxyethyl.

7. The compound of claim 1, wherein $R_4$ is a $C_1$-$C_6$ alkyl, phenyl, t-butyloxyl, a $C_2$-$C_6$ alkenyl, tetrahydrofuranyl, or tetrahydropyranyl.

8. The compound of claim 1, wherein $R_4$ is a pentyl, phenyl, t-butyloxyl, but-2-enyl, tetrahydrofuranyl, or tetrahydropyranyl.

9. A compound of formula (V) or (VI):

-continued (VI)

wherein
- R₁ is a hydrogen atom or a suitable protecting group for a hydroxyl group;
- R₂ is a hydrogen atom or a suitable protecting group for a hydroxyl group;
- R₃ is a hydrogen atom or a suitable protecting group for a hydroxyl group; and
- R₄ is a hydrogen atom, a $C_1$-$C_{20}$ alkyl linear or branched, $C_1$-$C_{20}$ acyl group, $C_1$-$C_{20}$ halogenated acyl group, $C_3$-$C_{12}$ cycloalkyl, $C_2$-$C_{20}$ alkenyl, $C_2$-$C_{20}$ alkynyl, $C_6$-$C_{12}$ aryl, $C_6$-$C_{20}$ aralkyl, $C_1$-$C_{20}$ alkyloxy $C_6$-$C_{20}$ alkylaryl, and
- R₅ is a hydrogen atom or a suitable protecting group for a hydroxyl group, said alkyl, cycloalkyl, alkenyl, alkynyl, aryl, aralkyl, alkylaryl, are unsubstituted or substituted with at least one substituent, each of said substituent(s) being chosen from F, Cl, Br, I, OH, SH, NH₂, NO₂, CN, CF₃, —SH, —OCH₂Ph, —OPh, —SCH₃, —SPh, —SCH₂Ph, —COOH, —COOR₆ in which R₆ is a $C_1$-$C_6$ alkyl, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{20}$ hydroxyalkyl, $C_6$-$C_{12}$ hydroxyaryl.

10. The compound of claim 9, wherein said suitable protecting group for a hydroxyl group is chosen from $C_1$-$C_{25}$ ethers, $C_1$-$C_{25}$ substituted methyl ethers, $C_1$-$C_{25}$ substituted ethyl ethers, $C_1$-$C_{25}$ acyl groups, $C_1$-$C_{25}$ halogenated acyl groups, $C_1$-$C_{25}$ substituted benzyl ethers, $C_1$-$C_{25}$ silyl ethers, $C_1$-$C_{25}$ esters, $C_1$-$C_{25}$ carbonates, and $C_1$-$C_{25}$ sulfonates.

11. The compound of claim 9, wherein said suitable protecting group for a hydroxyl group is chosen from methyl, methoxymethyl, benzyloxymethyl, tetrahydropyranyl, tetrahydrofuranyl, 2-(trimethylsilyl)ethoxymethyl, dioxanyl, 1-ethoxyethyl, 1-(2-chloroethoxy)ethyl, 2,2,2-trichloroethyl, t-butyl, allyl, propargyl, benzyl, p-methoxybenzyl, diphenylmethyl, triphenylmethyl, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl, benzylformate, methylcarbonyl, ethylcarbonyl, methoxymethylcarbonyl, trichloroethoxycarbonyl, benzylcarbonyl, benzyloxycarbonyl, allylsulfonyl, methanesulfonyl, and p-toluenesulfonyl.

12. The compound of claim 9, wherein R₁ is triethylsilyl.

13. The compound of claim 9, wherein R₂ is acetyl.

14. The compound of claim 9, wherein R₃ is ethoxyethyl.

15. The compound of claim 9, wherein R₄ is a $C_1$-$C_6$ alkyl, phenyl, t-butyloxyl, a $C_2$-$C_6$ alkenyl, tetrahydrofuranyl, or tetrahydropyranyl.

16. The compound of claim 9, wherein R₄ is a pentyl, phenyl, t-butyloxyl, but-2-enyl, tetrahydrofuranyl, or tetrahydropyranyl.

17. The compound of claim 9, wherein R₅ is triethylsilyl.

18. A process for preparing a compound of formula (II):

(II)

said process comprising reacting an oxidizing agent with a compound of formula (I):

(I)

wherein
- R₁ is a hydrogen atom or a suitable protecting group for a hydroxyl group; and
- R₂ is a hydrogen atom or a suitable protecting group for a hydroxyl group.

19. The process of claim 18, wherein said suitable protecting group for a hydroxyl group is chosen from $C_1$-$C_{25}$ ethers, $C_1$-$C_{25}$ substituted methyl ethers, $C_1$-$C_{25}$ substituted ethyl ethers, $C_1$-$C_{25}$ acyl groups, $C_1$-$C_{25}$ halogenated acyl groups, $C_1$-$C_{25}$ substituted benzyl ethers, $C_1$-$C_{25}$ silyl ethers, $C_1$-$C_{25}$ esters, $C_1$-$C_{25}$ carbonates, and $C_1$-$C_{25}$ sulfonates.

20. The process of claim 18, wherein said suitable protecting group for a hydroxyl group is chosen from methyl, methoxymethyl, benzyloxymethyl, tetrahydropyranyl, tetrahydrofuranyl, 2-(trimethylsilyl)ethoxymethyl, dioxanyl, 1-ethoxyethyl, 1-(2-chloroethoxy)ethyl, 2,2,2-trichloroethyl, t-butyl, allyl, propargyl, benzyl, p-methoxybenzyl, diphenylmethyl, triphenylmethyl, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl, benzylformate, methylcarbonyl, ethylcarbonyl, methoxymethyl arbonyl, trichloroethoxycarbonyl, benzylcarbonyl, benzyloxycarbonyl, allylsulfonyl, methanesulfonyl, and p-toluenesulfonyl.

21. The process of claim 18, wherein $R_1$ is triethylsilyl.

22. The process of claim 18, wherein $R_2$ is acetyl.

23. The process of claim 18, wherein said oxidizing agent is chosen from tetra-n-propylammonium perruthenate, Collin's reagent, pyridinium chlorochromate (PCC), pyridinium dichromate (PDC), $CrO_2$, activated methyl sulfoxide (Swern reagent), and John's reagent.

24. A process for converting 9-dihydro-13-acetylbaccatin III into a taxane derivative comprising the step of removing 10-acetyl group and oxidizing the C-9 and C-10 positions of the 9-dihydro-13-acetylbaccatin III.

25. The process of claim 24, wherein the oxidizing step is achieve by the addition of an oxidizing agent chosen from tetra-n-propylammonium perruthenate, Collin's reagent, PCC, PDC, $CrO_2$, activated methyl sulfoxide (Swern reagent), and John's reagent.

26. A process for preparing paclitaxel, docetaxel and a compound thereof comprising the steps of:
(a) protecting the C-7 hydroxy group of 9-dihydro-13-acetylbaccatin III with a suitable protecting group to obtain a protected product;
(b) deacetylating the 10-acetyl group of the protected product; and
(c) oxidizing the C-9 and C-10 hydroxy group of the protected product.

27. The process of claim 26, wherein the protecting group is chosen from benzyl, $C_1$-$C_{25}$ substituted benzyl, benzylformate, $C_1$-$C_{25}$ substituted benzylformate, tosyl, $C_1$-$C_{25}$ substituted tosyl, dihydropyranyl, methoxymethyl, benzoyl, $C_1$-$C_{25}$ substituted benzoyl, $C_1$-$C_{25}$ trialkylsilyl, 2-(trimethylsilyl)ethoxymethyl, benzyloxycarbonyl, triethylsilyl, triisopropylsilyl, dimethylisopropylsilyl, and t-butyldiphenylsilyl.

28. The process of claim 26, wherein the oxidizing step is achieved by the addition of an oxidizing reagent chosen from of tetra-n-propylammonium perruthenate, Collin's reagent, PDC, PCC, $CrO_2$ and activated methyl sulfoxide.

29. The process of claim 26, further comprising the step of deacetylating the C-13 position.

30. The process of claim 29, wherein the deacetylating step is achieved by the addition of an strong base chosen from n-BuLi, $CH_3Li$, $NaBH_4$, red-Al, and hydrazine monohydrate.

31. The process of claim 29, further comprising the step of reducing the C-10 ketone into C-10 hydroxyl group.

32. The process of claim 31, wherein the reducing the C-10 ketone step is achieved by the addition of an reduction agents chosen from Pd/C, $NaBH_4/CeCl_3$, $LiAlH_4$, and BINAP, and (s)-diam-BINAP.

33. A process for preparing a compound of formula 8:

comprising the step of reducing the C-10 ketone of a compound of formula 7:

34. The process of claim 33, wherein the reducing the C-10 ketone step is achieved by the addition of an reduction agents chosen from Pd/C, $NaBH_4/CeCl_3$, $LiAlH_4$, and BINAP, and (s)-diam-BINAP.

35. The process of claim 34, further comprising the step of deprotecting the C-7 position to obtain 10-deacetylbaccatin III.

36. The process of claim 29, further comprising the steps of adding a suitable side chain to the C-13 position, reducing C-10 and selectively deprotecting to obtain a desired product.

37. The process of claim 36, wherein the deprotection is done at the C-7 and 2' positions to obtain paclitaxel and docetaxel.

38. The process of claim 37, wherein the deprotection is achieved by addition of a deprotection agents chosen from diluted HCl, HF, and NaOCl.

39. The process of claim 36, wherein the side chain is chosen from (2R,3S)—N-benzoyl-O-(1-ethoxyethyl)-3-phenylisoserine; (3R,4S)-3-(1-ethoxyethoxy)-4-(phenyl)-N-benzoyl-2-azetidinone; (2R,3S)—N-boc-O-(1-ethoxyethyl)-3-phenylisoserine and (3R,4S)-3-(1-ethoxyethoxy)-4-(phenyl)-N-boc-2-azetidinone.

40. The process of claim 24, wherein said taxane derivative is paclitaxel or docetaxel.

* * * * *

UNITED STATES PATENT AND TRADEMARK OFFICE
CERTIFICATE OF CORRECTION

| | | |
|---|---|---|
| PATENT NO. | : 7,847,111 B2 | Page 1 of 1 |
| APPLICATION NO. | : 11/425034 | |
| DATED | : December 7, 2010 | |
| INVENTOR(S) | : Jian Liu | |

It is certified that error appears in the above-identified patent and that said Letters Patent is hereby corrected as shown below:

Title Page; item (73);
On the cover page of the above mentioned Letters Patent the assignee's name should read 6570763 Canada Inc., instead of Canada Inc.

Signed and Sealed this
Eighth Day of February, 2011

David J. Kappos
*Director of the United States Patent and Trademark Office*